US010441702B2

(12) United States Patent
Crawford et al.

(10) Patent No.: US 10,441,702 B2
(45) Date of Patent: Oct. 15, 2019

(54) MEDICAL FLUID TEMPERATURE CONTROL

(71) Applicant: Fresenius Medical Care Holdings, Inc., Waltham, MA (US)

(72) Inventors: William Scott Crawford, Palo Alto, CA (US); Robert Matthew Ohline, Redwood City, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 171 days.

(21) Appl. No.: 15/284,792

(22) Filed: Oct. 4, 2016

(65) Prior Publication Data

US 2018/0093031 A1    Apr. 5, 2018

(51) Int. Cl.
*A61M 1/28* (2006.01)
*A61M 1/16* (2006.01)

(52) U.S. Cl.
CPC ............ *A61M 1/28* (2013.01); *A61M 1/1623* (2014.02); *A61M 1/1629* (2014.02); *A61M 1/281* (2014.02); *A61M 2205/127* (2013.01); *A61M 2205/3368* (2013.01); *A61M 2205/3673* (2013.01)

(58) Field of Classification Search
CPC .... A61M 1/1623; A61M 1/1629; A61M 1/28; A61M 1/281; A61M 1/284; A61M 1/288; A61M 2205/04; A61M 2205/103; A61M 2205/106; A61M 2205/12; A61M 2205/127; A61M 2205/3368; A61M 2205/3569
See application file for complete search history.

(56) References Cited

U.S. PATENT DOCUMENTS

| | | | |
|---|---|---|---|
| 6,595,948 B2 | 7/2003 | Suzuki et al. | |
| 6,743,201 B1 | 6/2004 | Doenig et al. | |
| 6,764,761 B2 | 7/2004 | Eu et al. | |
| 7,935,074 B2* | 5/2011 | Plahey | A61M 1/28 210/646 |
| 2009/0012447 A1 | 1/2009 | Huitt et al. | |
| 2012/0323169 A1 | 12/2012 | Wiktor | |
| 2013/0165847 A1 | 6/2013 | Scarpaci et al. | |
| 2013/0310736 A1* | 11/2013 | Hedmann | A61M 1/28 604/29 |
| 2014/0018727 A1 | 1/2014 | Burbank et al. | |
| 2014/0018728 A1* | 1/2014 | Plahey | A61M 1/16 604/29 |
| 2014/0031631 A1 | 1/2014 | Hall et al. | |

(Continued)

FOREIGN PATENT DOCUMENTS

| | | |
|---|---|---|
| EP | 2532999 | 12/2012 |
| WO | 2011008858 | 1/2011 |
| WO | 2017065152 | 4/2017 |

OTHER PUBLICATIONS

International Search Report and Written Opinion in International Application No. PCT/US2017/052667, dated Feb. 6, 2018, 19 pages.

(Continued)

*Primary Examiner* — Quynh-Nhu H. Vu
(74) *Attorney, Agent, or Firm* — Fish & Richardson P.C.

(57) ABSTRACT

Devices, systems, and methods can be used to deliver temperature-controlled medical fluids to patients. For example, this disclosure provides devices, systems, and methods for controlling the temperature of dialysate delivered to a patient during a peritoneal dialysis treatment.

11 Claims, 6 Drawing Sheets

(56) References Cited

U.S. PATENT DOCUMENTS

| | | | | |
|---|---|---|---|---|
| 2014/0046248 A1* | 2/2014 | Fini | ............... | A61M 1/166 |
| | | | | 604/29 |
| 2014/0309612 A1* | 10/2014 | Smisson, III | ....... | A61M 1/0281 |
| | | | | 604/500 |
| 2015/0005699 A1 | 1/2015 | Burbank et al. | | |
| 2015/0057601 A1 | 2/2015 | Ly et al. | | |
| 2016/0101278 A1* | 4/2016 | Norris | ............... | A61M 1/166 |
| | | | | 604/29 |
| 2017/0157311 A1* | 6/2017 | Egley | ............... | A61M 1/282 |

OTHER PUBLICATIONS

PCT Invitation to Pay Additional Fees in International Application No. PCT/US2017/052667, dated Dec. 7, 2017, 14 pages.

\* cited by examiner

MEDICAL FLUID TEMPERATURE CONTROL

TECHNICAL FIELD

This invention relates to temperature control of medical fluids such as dialysate.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with sterile aqueous solution, referred to as PD solution or dialysate. The membranous lining of the patient's peritoneum acts as a natural semipermeable membrane that allows diffusion and osmosis exchanges to take place between the solution and the blood stream. These exchanges across the patient's peritoneum result in the removal waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle. It is advantageous for the dialysate temperature to approximate body temperature (37° C.) during a PD treatment. Dialysate that is too hot or too cold may be uncomfortable and/or hazardous to the patient.

SUMMARY

In one aspect, this disclosure is directed to a peritoneal dialysis machine that includes a console and one or more processors coupled to the console. The console includes a compartment configured to releasably receive a dialysis fluid cassette. The console also includes one or more thermoelectric modules arranged to be adjacent the cassette while the cassette is received by the compartment. The one or more thermoelectric modules are configured to effectuate energy transfer with a dialysis fluid in a fluid flow path of the cassette that is adjacent the one or more thermoelectric modules. The one or more processors coupled to the console are configured to control the one or more thermoelectric modules such that: (i) during a heating mode the one or more thermoelectric modules heat the dialysis fluid in the fluid flow path of the cassette and (ii) during a cooling mode the one or more thermoelectric modules cool the dialysis fluid in the fluid flow path of the cassette.

Such a peritoneal dialysis machine may optionally include one or more of the following features. The peritoneal dialysis machine may also include a fluid temperature sensor arranged to detect a temperature of the dialysis fluid. The one or more processors may be configured to control the one or more thermoelectric modules based on the temperature of the dialysis fluid detected by the fluid temperature sensor. The peritoneal dialysis machine may also include an ambient temperature sensor arranged to detect an ambient temperature around the peritoneal dialysis machine. The one or more processors may be configured to control the one or more thermoelectric modules based on the ambient temperature detected by the ambient temperature sensor. The fluid temperature sensor may be located to detect the temperature of the dialysis fluid prior to being affected by the one or more thermoelectric modules. The fluid temperature sensor may be located to detect the temperature of the dialysis fluid after being affected by the one or more thermoelectric modules. The peritoneal dialysis machine may also include a first fluid temperature sensor located to detect the temperature of the dialysis fluid prior to being affected by the one or more thermoelectric modules, and a second fluid temperature sensor located to detect the temperature of the dialysis fluid after being affected by the one or more thermoelectric modules. The one or more processors may be configured to control the one or more thermoelectric modules based on the temperatures of the dialysis fluid detected by the first fluid temperature sensor and the second fluid temperature sensor. The peritoneal dialysis machine may also include first and second movable piston heads. The first and second movable piston heads may be movable in a direction substantially perpendicular to the cassette. The cassette may include a base defining an opening and a membrane attached to the base covering the opening. The membrane together with the base may define: (i) a fluid pump chamber, (ii) a fluid flow path that leads from the fluid pump chamber to an inlet of the cassette, and (iii) a fluid flow path that leads from the fluid pump chamber to an outlet of the cassette. A portion of the membrane overlying the fluid pump chamber may be moveable relative to the base such that the volume of the fluid pump chamber can be changed by applying a force to the portion of the membrane overlying the fluid pump chamber. The peritoneal dialysis machine may be adapted to be connected to a supply of water and to a source of concentrate and to generate the dialysis fluid using the water and the concentrate.

In another aspect, this disclosure is directed to a peritoneal dialysis system including a dialysis fluid cassette configured to contain a dialysis fluid, and a peritoneal dialysis machine comprising a compartment configured to releasably receive the cassette. The peritoneal dialysis machine includes one or more thermoelectric modules arranged to be adjacent the cassette while the cassette is received by the compartment and to effectuate energy transfer with a dialysis fluid in a fluid flow path of the cassette that is adjacent the one or more thermoelectric modules, and one or more processors coupled to the console and configured to control the one or more thermoelectric modules such that: (i) during a heating mode the one or more thermoelectric modules heat the dialysis fluid in the fluid flow path of the cassette and (ii) during a cooling mode the one or more thermoelectric modules cool the dialysis fluid in the fluid flow path of the cassette.

Such a peritoneal dialysis system may optionally include one or more of the following features. The fluid flow path may be a serpentine fluid flow path. The peritoneal dialysis system may also include a fluid temperature sensor arranged to detect a temperature of the dialysis fluid. The one or more processors may be configured to control the one or more thermoelectric modules based on the temperature of the dialysis fluid detected by the fluid temperature sensor. The peritoneal dialysis system may also include an ambient temperature sensor arranged to detect an ambient temperature around the peritoneal dialysis machine. The one or more processors may be configured to control the one or more thermoelectric modules based on the ambient temperature detected by the ambient temperature sensor. The peritoneal dialysis system may also include first and second movable piston heads. The first and second movable piston heads may be movable in a direction substantially perpendicular to the cassette. The peritoneal dialysis machine may be adapted to be connected to a supply of water and to a source of concentrate and to generate the dialysis fluid using the water and the concentrate.

In another aspect, this disclosure is directed to a method of controlling a fluid temperature of a dialysis fluid supplied from a peritoneal dialysis system. Such a method may include: detecting, by a control system of the peritoneal dialysis system, an ambient temperature around the peritoneal dialysis system; determining, by the control system and based on the ambient temperature, a target fluid temperature of the dialysis fluid; detecting, by the control system, an actual fluid temperature of the dialysis fluid; determining, by the control system and based on the target fluid temperature and the actual fluid temperature, one or more electrical supply energy parameters; and delivering, by the control system, electrical energy corresponding to the one or more electrical energy supply parameters to one or more thermoelectric modules of the peritoneal dialysis system. The delivering causes cooling of the dialysis fluid by the one or more thermoelectric modules.

Such a method of controlling a fluid temperature of a dialysis fluid supplied from a peritoneal dialysis system may optionally include one or more of the following features. The method may also include delivering, by the control system, electrical energy corresponding to the one or more electrical energy supply parameters to one or more thermoelectric modules of the peritoneal dialysis system. The delivering may cause heating of the dialysis fluid by the one or more thermoelectric modules. The cooling may include cooling the dialysis fluid in a fluid flow path of a cassette coupled with the peritoneal dialysis system. The target fluid temperature may be less than 37° C. when the ambient temperature is greater than 37° C. The actual fluid temperature may be greater than the target fluid temperature. The dialysis fluid may be a dialysate. The method may also include generating the dialysis fluid by introducing one or more concentrates into a supply of water.

In another aspect, this disclosure is directed to a device for controlling a temperature of a dialysis fluid delivered to a patient. The device includes: a housing configured to releasably mate with a conduit containing the dialysis fluid; one or more thermoelectric modules coupled to the housing and arranged to be adjacent the conduit while the conduit is mated with the housing and to effectuate energy transfer with the dialysis fluid in the conduit; and a temperature sensor arranged to detect a fluid temperature of the dialysis fluid. The device is configured to be positioned at any of multiple difference locations along the conduit.

Such a device for controlling a temperature of a dialysis fluid delivered to a patient may optionally include one or more of the following features. The temperature sensor may be coupled to the housing. The one or more thermoelectric modules may be configured to be operated: (i) in a heating mode during which the one or more thermoelectric modules heat the dialysis fluid and (ii) in a cooling mode during which the one or more thermoelectric modules cool the dialysis fluid. The conduit may be a flexible tube. The housing may be configured to releasably mate with the flexible tube in a serpentine pattern. The device may be positioned within 12 inches of an end of the conduit that connects to a patient.

In another aspect, this disclosure is directed to a peritoneal dialysis system including: a dialysis fluid cassette configured to contain a dialysis fluid; a tube extending from the cassette and configured for delivering the dialysis fluid to a patient; a peritoneal dialysis machine comprising a compartment configured to releasably receive the cassette; and a temperature control device for controlling a temperature of the dialysis fluid delivered to a patient. The temperature control device includes: a housing configured to releasably mate with the tube; one or more thermoelectric modules coupled to the housing and arranged to be adjacent the tube while the tube is mated with the housing and to effectuate energy transfer with the dialysis fluid in the tube; and a temperature sensor arranged to detect a fluid temperature of the dialysis fluid. The temperature control device is separate from the peritoneal dialysis machine.

Such a peritoneal dialysis system may optionally include one or more of the following features. The temperature sensor may be coupled to the housing. The temperature control device may be electrically coupled with the peritoneal dialysis machine such that energy activating the one or more thermoelectric modules is received from the peritoneal dialysis machine and a temperature signal from the temperature sensor is transmitted to the peritoneal dialysis machine. The temperature control device may be independent from the peritoneal dialysis machine such that the temperature control device is not in electrical communication with the peritoneal dialysis machine. The one or more thermoelectric modules may be configured to be operated: (i) in a heating mode during which the one or more thermoelectric modules heat the dialysis fluid and (ii) in a cooling mode during which the one or more thermoelectric modules cool the dialysis fluid. The temperature control device may be configured to releasably mate with the tube being configured in a serpentine pattern. The temperature control device may be positioned within 12 inches of an end of the tube that connects to the patient. The peritoneal dialysis machine may be adapted to be connected to a supply of water and to a source of concentrate and to generate the dialysis fluid using the water and the concentrate.

In another aspect, this disclosure is directed to a method of controlling a fluid temperature of a dialysis fluid supplied to a patient from a peritoneal dialysis system comprising a peritoneal dialysis machine and a temperature control device that is separate from the peritoneal dialysis machine. The method includes: detecting, by a control system of the peritoneal dialysis machine and using a temperature sensor, a fluid temperature of the dialysis fluid; determining, by the control system and based on the fluid temperature, one or more electrical supply energy parameters; and delivering, by the control system, electrical energy corresponding to the one or more electrical energy supply parameters to one or more thermoelectric modules of the temperature control device.

Such a method of controlling a fluid temperature of a dialysis fluid supplied to a patient may optionally include one or more of the following features. The temperature sensor may be located at the temperature control device or between the temperature control device and the patient. The delivering may cause: (i) heating of the dialysis fluid by the one or more thermoelectric modules while the fluid temperature is less than 37° C. and (ii) cooling of the dialysis fluid by the one or more thermoelectric modules while the fluid temperature is greater than 37° C. The dialysis fluid may be a dialysate. The temperature control device may be positioned within 24 inches of an end of a tube from the peritoneal dialysis machine that connects to the patient. The method may also include generating the dialysis fluid by introducing one or more concentrates into a supply of water.

Embodiments can include one or more of the following advantages.

In some embodiments, the dialysis system regulates the temperature of dialysis solution being delivered to a patient to ensure that the dialysis solution that is delivered to the patient is at a safe and comfortable temperature.

In certain embodiments, the dialysis system is configured to cool dialysis solution that exceeds a desired temperature (e.g., due to high ambient temperature) prior to being delivered to the patient. The dialysis system can, for example, include a thermoelectric module that can be operated to cool the dialysis solution as it flows to the patient. Such an arrangement can help to ensure that the dialysis solution that is delivered to the patient is at a safe and comfortable temperature even when the ambient temperature exceeds the desired temperature of the fluid. This can be particularly beneficial for dialysis systems that are operated in homes or clinics in warm climates that do not have air conditioning.

In some embodiments, the dialysis system is arranged to heat or cool dialysis solution immediately prior to the dialysis solution entering the patient. The dialysis system can, for example, include a temperature control device that is separate from the dialysis machine and that can be positioned within 24 inches of an end of a fluid delivery line that connects to the patient. Heating or cooling the dialysis solution immediately prior to the dialysis solution entering the patient in this way can help to reduce the impact of ambient temperature on the heated solution and thus help to ensure that the dialysis solution is delivered to the patient at a desired temperature or within a desired temperature range.

In some embodiments, the dialysis system is configured to heat and cool dialysis solution on a real-time basis as the dialysis solution is being supplied to the patient. Hence, the potential for treatment delays while waiting for dialysis solution to be adjusted to a target temperature is advantageously reduced in some cases.

The details of one or more embodiments are set forth in the accompanying drawings and the description below. Other aspects, features, and advantages will be apparent from the description and drawings, and from the claims.

DETAILED DESCRIPTION

This disclosure is directed to devices, systems, and methods for delivering temperature-controlled dialysis solution to patients. For example, this disclosure provides devices, systems, and methods for controlling the temperature of dialysate delivered to a patient during a peritoneal dialysis ("PD") treatment.

Figure 1:
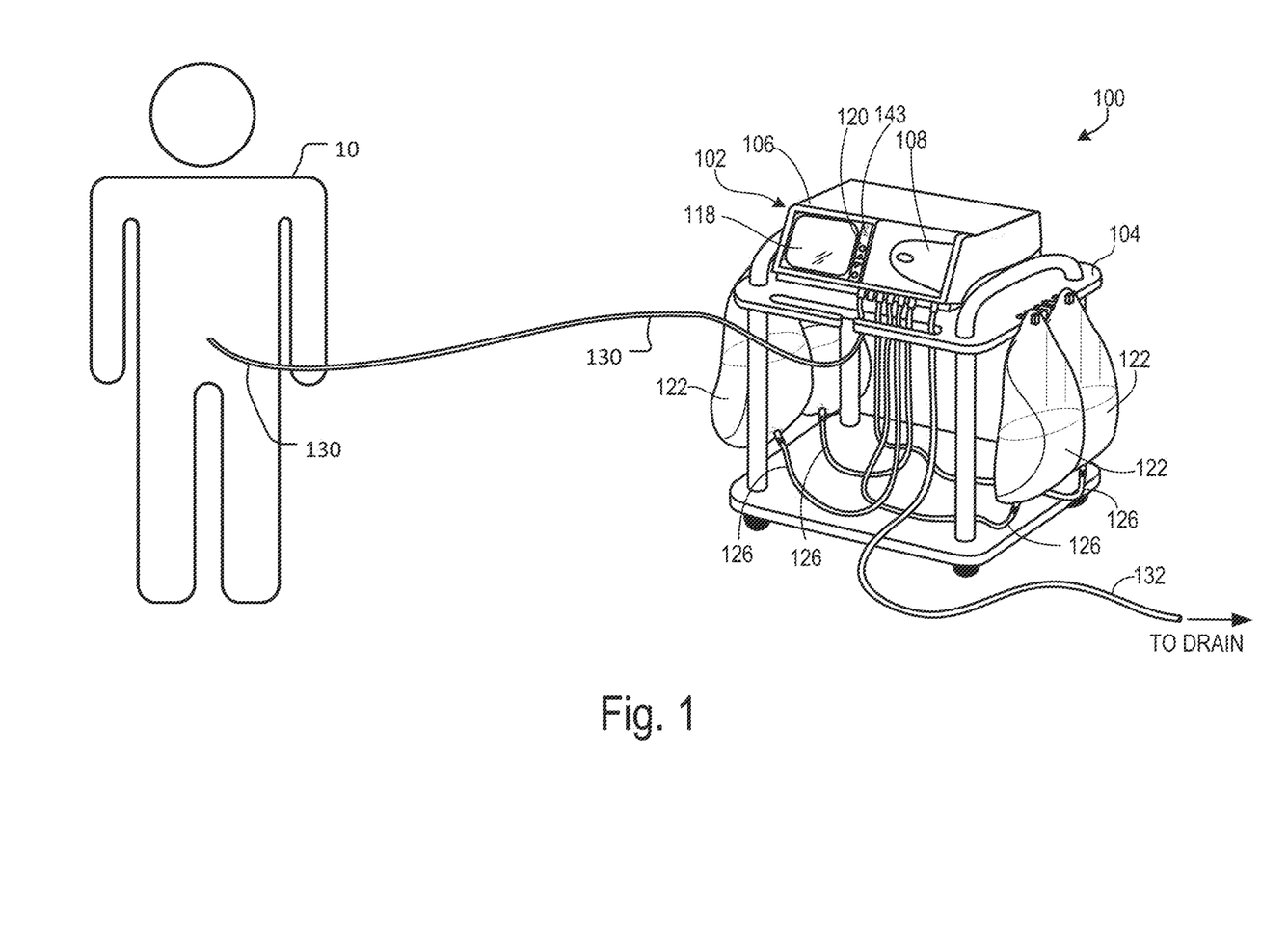
FIG. 1 is a perspective view of a patient receiving a peritoneal dialysis ("PD") treatment using a PD system.
Figure 2:
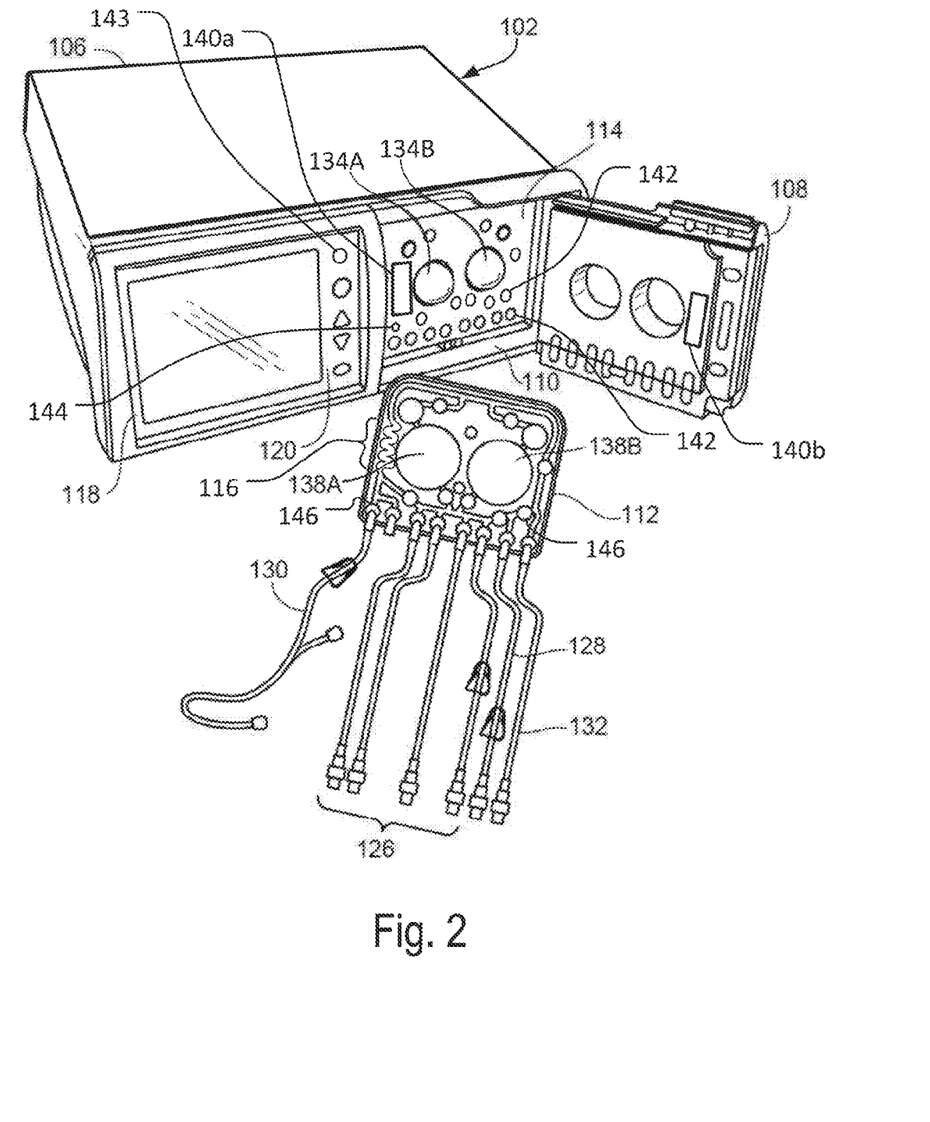
FIG. 2 is a perspective view of a PD machine and PD cassette of the PD system of FIG. 1. A door of the PD machine is in the open position to show the inner surfaces of the PD machine that interface with the PD cassette during use.

Referring to FIG. 1, a PD system 100 can provide a PD treatment to a patient 10. The PD system 100 includes a PD machine (also referred to as a "PD cycler") 102 seated on a cart 104. Referring also to FIG. 2, the PD machine 102 includes a console 106, a door 108, and a cassette interface 110 that receives a disposable PD cassette 112 when the cassette 112 is positioned within a cassette enclosure 114 formed between the cassette interface 110 and the closed door 108. The PD machine 102 also includes a touch screen 118 and additional control buttons 120 that can be operated by a user (e.g., the patient 10) to allow, for example, set-up, initiation, and/or termination of a PD treatment.

PD solution bags 122 are suspended from fingers on the sides of the cart 104. The PD solution bags 122 are connected to the cassette 112 via PD solution bag lines 126. The PD solution bag lines 126 can be used to pass PD solution from PD solution bags 122 to the cassette 112 during use. In addition, a patient line 130 and a drain line 132 are connected to the cassette. The patient line 130 can be connected to a patient's abdomen via a catheter and can be used to pass PD solution back and forth between the cassette 112 and the patient during use. The drain line 132 can be connected to a drain or drain receptacle and can be used to pass PD solution from the cassette 112 to the drain or drain receptacle during use.

As shown in FIG. 2, the PD machine 102 includes pistons with substantially hemispherical piston heads 134A, 134B that can be translated perpendicular to the major plane defined by the cassette 112. When the cassette 112 is positioned within the cassette enclosure 114 with the door 108 closed, the piston heads 134A, 134B of the PD machine 102 align with pump chambers 138A, 138B of the cassette 112. Movements of the piston heads 134A, 134B thereby interact with the cassette 112 to force fluid out of the pump chambers 138A, 138B and to draw fluid into the pump chambers 138A, 138B. In other words, movements of the piston heads 134A, 134B can pump medical fluids through the cassette 112. For example, dialysate from the PD solution bags 122 can be drawn into the cassette 112 and forced out of the cassette 112 through the patient line 130 by the pumping action of the movements of the piston heads 134A, 134B.

Still referring to FIG. 2, the PD machine 102 also includes multiple inflatable members 142 positioned in the cassette interface 110. The inflatable members 142 align with depressible dome regions 146 of the cassette 112 when the cassette 112 is positioned within the cassette enclosure 114. While only two of the inflatable members 142 are labeled in FIG. 2, it should be understood that the PD machine 102 includes an inflatable member associated with each of the depressible dome regions 146 of the cassette 112. The inflatable members 142 act as valve actuators to direct fluid through the cassette 112 in a desired manner during use. In particular, the inflatable members 142 bulge outward beyond the surface of cassette interface 110 and into contact with the depressible dome regions 146 of the cassette 112 when inflated, and retract out of contact with the cassette 112 when deflated. By inflating certain inflatable members 142 to depress their associated dome regions 146 on the cassette 112, certain fluid flow paths within the cassette 112 can be blocked off. Thus, fluid can be pumped through the cassette 112 by actuating the piston heads 134A, 134B, and can be guided along desired flow paths within the cassette 112 by selectively inflating and deflating the inflatable members 142.

The cassette 112 and the PD machine 102 include various other features not described here. Further details regarding the cassette 112 and the PD machine 102 and its various components can be found in U.S. Pat. No. 7,935,074, which is incorporated in its entirety by reference herein.

It is advantageous for the dialysate temperature supplied to a patient to approximate body temperature (37° C.) during a PD treatment. To that end, the PD machine 102 is configured for heating and cooling the dialysate to a target temperature. For example, the PD machine 102 includes a first energy transfer element 140a and a second energy transfer element 140b. The energy transfer elements 140a, 140b are coupled to the cassette interface 110 and door 108, respectively, in locations where the energy transfer elements 140a, 140b are adjacent to the cassette 112 while the cassette 112 is received by the cassette enclosure 114. Moreover, in the embodiment depicted in FIG. 2, the energy transfer elements 140a, 140b are adjacent to the cassette 112 at a portion 116 of the fluid flow path defined by the cassette 112 that is configured in a serpentine pattern. The serpentine pattern of the portion 116 may facilitate enhanced energy transfer between the dialysate and the energy transfer elements 140a, 140b as compared to a linear flow pattern.

In the depicted embodiment, the energy transfer elements 140a, 140b are thermoelectric modules. Some types of such thermoelectric modules exploit a phenomenon known as the Peltier effect to move heat from one side of the energy transfer elements 140a, 140b to the other side of the energy transfer elements 140a, 140b. In this process, when an electrical current flows through the energy transfer elements 140a, 140b, one side of the energy transfer elements 140a, 140b becomes cold, and the other side of energy transfer elements 140a, 140b becomes hot. Reversing the direction of the electrical current flowing through the energy transfer elements 140a, 140b also reverses which side of the energy transfer elements 140a, 140b becomes hot and which side becomes cold. Hence, the energy transfer elements 140a, 140b can be used to heat the dialysate and to cool the dialysate. Thermoelectric modules are advantageously compact, have no moving parts, and require only a supply of electrical current to perform their function.

The PD machine 102 is configured to heat and cool the dialysate in a controlled fashion. To that end, the PD machine 102 includes, at least, an ambient temperature sensor 143 and a fluid temperature sensor 144. The temperature sensors 143, 144 can be a variety of different types of sensors such as, but not limited to, resistive temperature devices, thermistors, thermocouples, and infrared sensors. The ambient temperature sensor 143 is arranged to detect an ambient temperature (e.g., a room temperature or air temperature) around the PD machine 102. The fluid temperature sensor 144 is arranged to detect a temperature of the dialysate within the cassette 112. In the depicted embodiment, the fluid temperature sensor 144 is located adjacent to the cassette 112 near where the dialysate exits the cassette 112 and enters the patient line 130. Locating the fluid temperature sensor 144 near the exit of the cassette 112 provides an accurate temperature reading of the dialysate leaving the PD machine 102.

The PD machine 102 also includes a control system (e.g., one or more processors, computer memory, executable instructions, sensors, electrical circuitry, user-interface components, etc.) that is configured to control operations of the PD machine 102. For example, the control system of the PD machine 102 is configured to control and modulate the supply of electrical energy to the energy transfer elements 140a, 140b. The control system of the PD machine 102 can control the supply of electrical energy to the energy transfer elements 140a, 140b based on signals indicative of temperatures detected by the temperature sensors 143, 144. For example, the electrical energy supplied to the energy transfer elements 140a, 140b can be controlled to modulate the temperature of the dialysate (heat or cool) to a target temperature as measured by the fluid temperature sensor 144. In such a case, a signal from the fluid temperature sensor 144 that indicates the detected temperature of the dialysate is received by the control system of the PD machine 102. The control system of the PD machine 102 can then compare the measured temperature of the dialysate to the target temperature of the dialysate. The difference between the measured temperature and the target temperature can then be used by the control system of the PD machine 102 to determine parameters (e.g., current, voltage, polarity) of the electrical energy to be supplied to the energy transfer elements 140a, 140b in attempt to achieve the target temperature. This technique provides closed-loop control of the dialysate temperature by the control system of the PD machine 102.

The control system of the PD machine 102 can be configured to determine a target temperature (e.g., as measured by the fluid temperature sensor 144) to result in the delivery of dialysate at about 37° C. to the patient. With the objective being to deliver 37° C. dialysate to the patient, the control system of the PD machine 102 can use the ambient temperature measured by the ambient temperature sensor 143 to determine the target temperature for the dialysate as it exits the PD machine 102. Such a target temperature for the dialysate (e.g., as measured by the fluid temperature sensor 144) can be determined based on the anticipated change in dialysate temperature as the dialysate flows in the patient line 130 from the PD machine 102 to the patient 10. For example, if the ambient temperature is 20° C., dialysate flowing in the patient line 130 at about 37° C. will tend to cool before reaching the patient. Therefore, the target temperature of the dialysate (e.g., as measured by the fluid temperature sensor 144) can be established at greater than 37° C. to compensate for the heat loss in the patient line 130. Conversely, if the ambient temperature is 40° C., the dialysate flowing in the patient line 130 at about 37° C. will tend to warm before reaching the patient. Therefore, the target temperature of the dialysate (e.g., as measured by the fluid temperature sensor 144) can be established at less than 37° C. to compensate for the heat gain in the patient line 130. Hence, the control system of the PD machine 102 can determine a target temperature for the dialysate by detecting the ambient temperature (as measured by the ambient temperature sensor 143) and using an estimate of the heat to be transferred to or from the dialysate as the dialysate flows in the patient line 130 from the PD machine 102 to the patient.

In some embodiments, the target temperature for the dialysate (e.g., as measured by the fluid temperature sensor 144) can be additionally or alternatively determined by measuring the temperature of the spent dialysate in the drain line 132 at a distance from the patient 10 equal to the length of the patient line 130. The initial fluid temperature, as it exits the patient 10, can be assumed to be 37° C., so the temperature change of the fluid down the length of the drain line 132 will tend to indicate the heat transferred into or out of the fluid, and provide a means of determining the target temperature for the dialysate as it exits the PD machine 102.

Still referring to FIGS. 1 and 2, during a PD treatment the patient line 130 is connected to the abdomen of the patient 10. The drain line 132 is connected to a drain or drain receptacle. The PD treatment typically begins by emptying the patient 10 of spent PD solution that remains in the patient's abdomen from the previous treatment. To do this, the pump of the PD machine 102 is activated to cause the piston heads 134A, 134B to reciprocate and selected inflatable members 142 are inflated to cause the spent PD solution to be drawn into the pump chambers 138A, 138B of the cassette 112 from the patient, and then pumped from the pump chambers 138A, 138B to the drain via the drain line 132. The PD machine 102 is typically used in an alternating pumping mode in which one piston head is protracted while the other piston head is retracted. Thus, as fluid is drawn into one pumping chamber, fluid is simultaneously expelled from the other pumping chamber.

After draining the spent PD solution from the patient 10, temperature-controlled PD solution (dialysate) is transferred to the patient 10. To do this, the pump of the PD machine 102 is activated to cause the piston heads 134A, 134B to reciprocate and certain inflatable members 142 of the PD machine 102 are inflated to cause PD solution from a PD solution bag 122 to be drawn into the pump chambers 138A, 138B of the cassette 112. While the piston heads 134A, 134B are causing the PD solution to flow through the cassette 112, the energy transfer elements 140a, 140b can be energized appropriately to heat or cool the PD solution to a target temperature as described above. The temperature-controlled PD solution flows from the cassette 112 to the patient via the patient line 130. The temperature of the dialysate as it reaches the patient 10 is intended to be about 37° C.

Once the PD solution has been pumped from the cassette 112 to the patient 10, the PD solution is allowed to dwell within the patient 10 for a period of time. During this dwell period, toxins cross the peritoneum into the PD solution from the patient's blood.

After the PD solution has dwelled within the patient 10 for the desired period of time, the spent PD solution is pumped from the patient 10 to the drain via lines 130, 132. Then, another quantity of temperature-controlled PD solution is pumped through the cassette 112 to the patient 10 where it dwells for a desired period of time. These steps are repeated with the PD solution from two of the three remaining PD solution bags 122. The PD solution from the last PD solution bag 122 is typically delivered to the patient 10 and left in the patient until the subsequent PD treatment.

Figure 3:
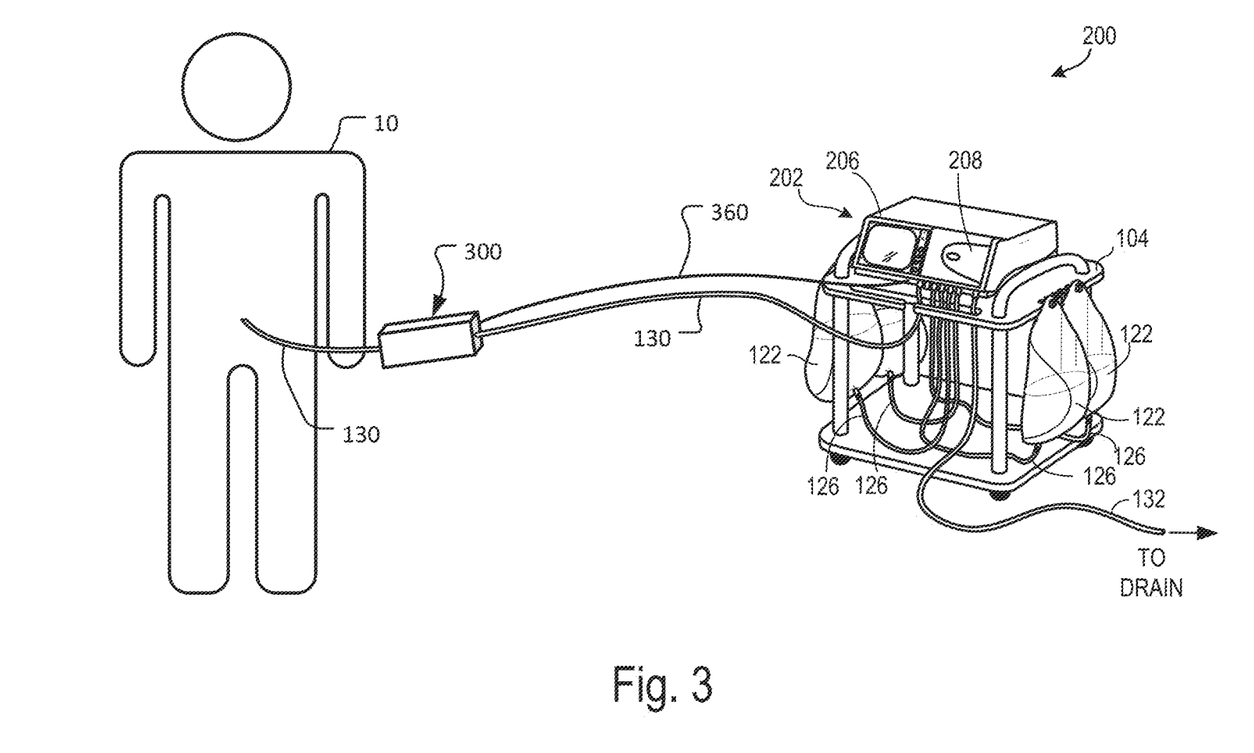
FIG. 3 is a perspective view of a patient receiving a PD treatment using another PD system, which includes a medical fluid temperature control device that is separate from the PD machine.

Referring to FIG. 3, another PD system 200 includes a PD machine 202, a cassette (not visible), and a temperature control device 300. The PD machine 202 supplies dialysate to a patient 10. The temperature control device 300 is releasably coupled with the patient line 130 such that it can heat and cool the dialysate delivered from the PD machine 202 to ensure that the temperature of the dialysate received by the patient is about 37° C.

In the depicted arrangement, the temperature control device 300 is located near the patient 10. Therefore, the dialysate will experience minimal heat loss or gain in the short portion of the patient line 130 between the temperature control device 300 and the patient 10. As a result, the temperature of the dialysate exiting the temperature control device 300 will be very close to the temperature of the dialysate entering the patient 10. Because of this, compensation for ambient temperature is generally not necessary in the context of the PD system 200. In some embodiments, the length of the patient line 130 from the exit of the temperature control device 300 to the connection with the patient 10 is about 12 inches or less (30.5 cm or less), about 18 inches or less (45.7 cm or less), about 24 inches or less (61.0 cm or less), or about 36 inches or less (91.4 cm or less). The temperature control device 300 can be releasably attached anywhere along the patient line 130.

The PD machine 202 includes a console 206 and a door 208 to a cassette interface. The PD machine 202 is designed analogous to the PD machine 102 described above, except that the PD machine 202 does not include the energy transfer elements 140a, 140b and the temperature sensors 143, 144. The separate temperature control device 300 is used instead.

The temperature control device 300 is in electrical communication with the PD machine 202 via a cable 360. As described further below, a signal representative of the dialysate temperature measured at the temperature control device 300 can be transferred to the PD machine 202 via the cable 360. Further, electrical energy from the PD machine 202 can be supplied to one or more energy transfer elements in the temperature control device 300 to heat and cool dialysate in the patient line 130. The temperature control device 300 is configured to releasably receive the patient line 130.

Figure 4:
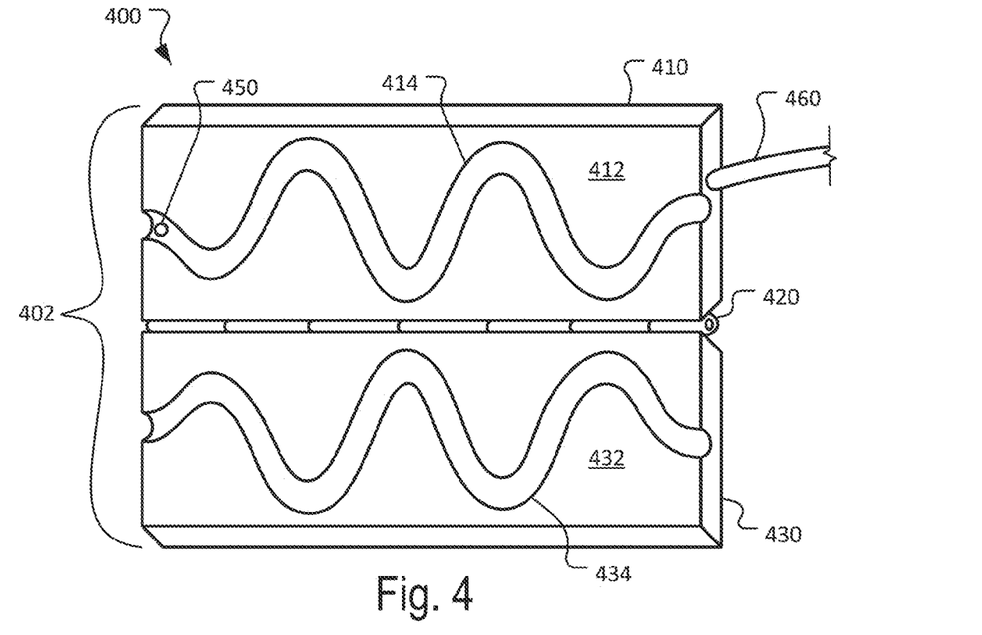
FIG. 4 is a perspective view of a medical fluid temperature control device.

Referring also to FIG. 4, in some embodiments the temperature control device 300 can be configured like the depicted temperature control device 400. The temperature control device 400 includes a housing 402 made up of a first housing portion 410 and a second housing portion 430. The first housing portion 410 and the second housing portion 430 are pivotably coupled to each other by a hinge 420. A temperature sensor 450 is coupled to the housing 402. A cable 460 extends from the housing 402 to the PD machine 202.

In the depicted arrangement, the housing 402 is open. That is, the housing portions 410, 430 are pivoted away from each other. The housing 402 can be closed by pivoting the first housing portion 410 into opposition with the second housing portion 430. In such a closed arrangement, a face 412 of the first housing portion 410 will be generally opposed to a face 432 of the second housing portion 430.

The housing portions 410, 430 each define serpentine grooves 414, 434 that are sized to receive the patient line 130. In some embodiments, the serpentine grooves 414, 434 have semicircular cross-sectional shapes so that each serpentine groove 414, 434 receives about ½ of the circular cross-section of the patient line 130. The serpentine grooves 414, 434 can be sized and arranged to avoid kinking of the patient line 130.

To couple the patient line 130 with the temperature control device 400, the patient line 130 can be placed within one of the serpentine grooves 414, 434, and then the first and second housing portions 410, 430 can be pivoted closed to capture the patient line 130 therebetween.

One or both of the housing portions 410, 430 can include one or more thermoelectric modules that are arranged adjacent the patient line 130 while the patient line 130 is received within the temperature control device 400 in the closed configuration. Accordingly, the one or more thermoelectric modules can effectuate energy transfer with dialysate within the patient line 130. The one or more thermoelectric modules that are arranged adjacent the patient line 130 can selectively heat and cool the dialysate within the patient line 130. In some embodiments, the one or more thermoelectric modules are discrete portions of the faces 412, 432 arranged along one or both of the serpentine grooves 412, 432. In some embodiments, the one or more thermoelectric modules comprise the entirety of one or both of the faces 412, 432.

The temperature sensor 450 is arranged to detect the fluid temperature of dialysate within the patient line 130. In the depicted embodiment, the temperature sensor 450 is coupled to the housing 402 near where the patient line 130 exits the housing 402 (at a patient-side of the housing 402).

The cable 460 conveys the electrical signal from the temperature sensor 450 to the control system of the PD machine 202. In addition, the cable conveys electrical energy from the control system of the PD machine 202 to the one or more energy transfer elements in the temperature control device 400 to modulate the heating and cooling of the dialysate in the patient line 130.

The temperature control device 400 can operate like the dialysate heating and cooling system of the PD machine 102 described above. That is, the control system of the PD machine 202 is configured to control and modulate the supply of electrical energy to the energy transfer elements of the temperature control device 400 to attain a target temperature. The control system of the PD machine 202 can base such supply of electrical energy to the energy transfer elements on the signal from the temperature sensor 450 that is indicative of the actual dialysate temperature. For example, the electrical energy supplied to the energy transfer elements of the temperature control device 400 can be controlled to modulate the temperature of the dialysate (heat or cool) to a target temperature (e.g., 37° C.) as measured by the fluid temperature sensor 450. In other words, the control system of the PD machine 202 can compare the temperature of the dialysate as measured by the temperature sensor 450 to the target temperature of the dialysate. The difference between the measured dialysate temperature and the target dialysate temperature can then be used by the control system of the PD machine 202 to determine parameters (e.g., current, voltage, polarity) of the electrical energy to be supplied to the energy transfer elements of the temperature control device 400 to achieve the target temperature. This technique provides closed-loop control of the dialysate temperature by the control system of the PD machine 202 in conjunction with the temperature control device 400.

Figure 5:
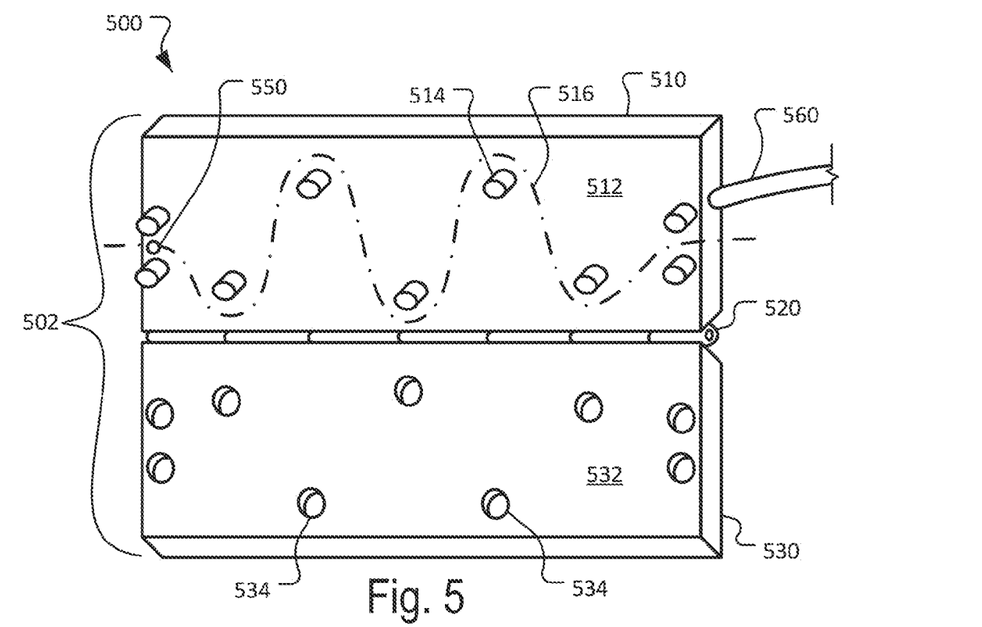
FIG. 5 is a perspective view of another medical fluid temperature control device.

Referring also to FIG. 5, in some embodiments, the temperature control device 300 is configured like the depicted temperature control device 500. The temperature control device 500 includes a housing 502 made up of a first housing portion 510 and a second housing portion 530. The first housing portion 510 and the second housing portion 530 are pivotably coupled to each other by a hinge 520. A temperature sensor 550 is coupled to the housing 502. A cable 560 extends from the housing 502 to the PD machine 202.

The temperature control device 500 is analogous to the temperature control device 400 except the faces 512, 532 of the temperature control device 500 do not define serpentine grooves like the temperature control device 400. Instead, the first housing portion 510 includes multiple projections 514 and the second housing portion 530 includes corresponding multiple indentations 534 that receive the multiple projections 514.

To couple the patient line 130 with the temperature control device 500, the patient line 130 can be threaded through the projections 514 in a serpentine arrangement (as depicted by the broken line 516), and then the first and second housing portions 510, 530 can be pivoted into opposition to each other (i.e., the closed configuration) to capture the patient line 130 therebetween. The projections 514 and corresponding indentations 534 can be sized and arranged to avoid kinking of the patient line 130.

Like the temperature control device 400, one or both of the housing portions 510, 530 can include one or more thermoelectric modules that are arranged adjacent the patient line 130 while the patient line 130 is received within the temperature control device 500 in the closed configuration. Accordingly, the one or more thermoelectric modules that are arranged adjacent the patient line 130 can effectuate energy transfer with dialysate within the patient line 130. The one or more thermoelectric modules of the temperature control device 500 can thereby heat and cool the dialysate within the patient line 130.

Figure 6:
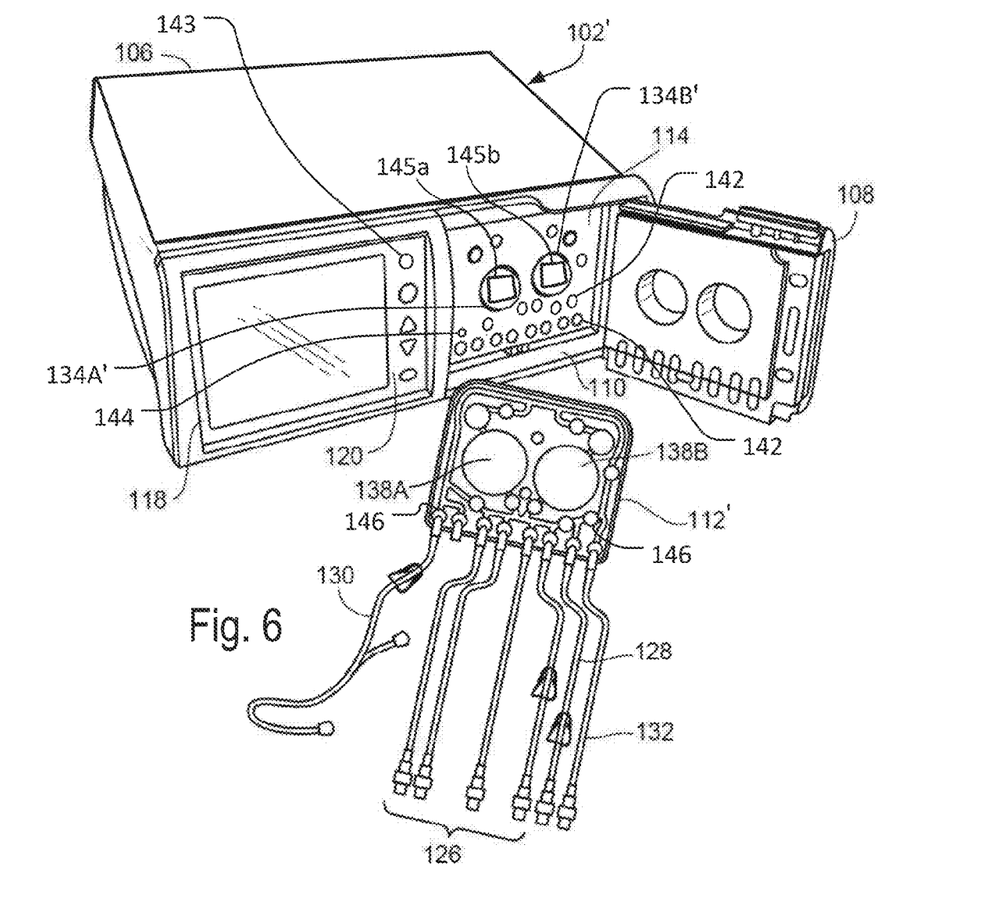
FIG. 6 is a perspective view of another PD system embodiment that can be used to treat a patient as depicted in FIG. 1.
Figure 7:
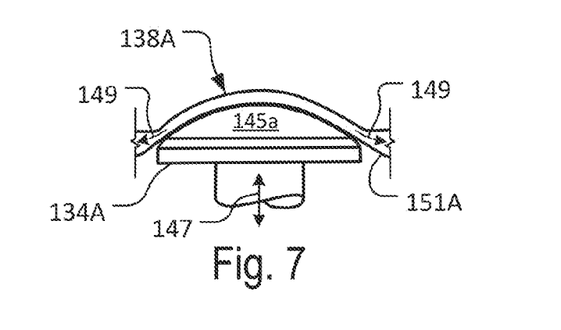
FIG. 7 is a partial top view of the PD system of FIG. 6 showing a piston and a cassette pump chamber.

FIGS. 6 and 7 depict another example PD machine 102'. Like the PD machine 102 described above in reference to FIG. 2, the PD machine 102' is configured for delivering temperature-controlled dialysis solution to patients. In the depicted embodiment, the PD machine 102' is structurally and functionally analogous to the PD machine 102 except for the configuration of the respective energy transfer elements. That is, while the PD machine 102 includes the energy transfer elements 140*a*, 140*b* that are coupled to the cassette interface 110 and door 108, respectively, the PD machine 102' includes energy transfer elements 145*a* and 145*b* that are located on the substantially hemispherical piston heads 134A' and 134B'.

The piston heads 134A', 134B' can be translated perpendicular (as depicted by double arrow 147 in FIG. 7) to the major plane defined by the cassette 112. When the cassette 112' is positioned within the cassette enclosure 114 with the door 108 closed, the piston heads 134A', 134B' of the PD machine 102' align with pump chambers 138A, 138B of the cassette 112'. Movements of the piston heads 134A', 134B' thereby interact with the cassette 112' to force fluid out of the pump chambers 138A, 138B (as depicted by arrows 149 in FIG. 7), and to draw fluid into the pump chambers 138A, 138B. In other words, reciprocating movements of the piston heads 134N, 134B' can pump medical fluids through the cassette 112'. For example, dialysate from the PD solution bags 122 (FIG. 1) can be drawn into the cassette 112' and forced out of the cassette 112' through the patient line 130 by the pumping action of the movements of the piston heads 134N, 134B'.

In addition to the pumping action provided by the piston heads 134N, 134B', the energy transfer elements 145*a*, 145*b* located on the piston heads 134N, 134B' can be used to heat or cool the fluid within the pump chambers 138A, 138B of the cassette 112'. The pump chambers 138A, 138B are partially defined by a compliant film 151A (FIG. 7), 151B (not shown) that makes contact with the energy transfer elements 145*a*, 145*b* located on the piston heads 134N, 134B'. Heat energy can be transferred, for example, between the energy transfer element 145*a* and the fluid in pump chamber 138A, via the compliant film 151A. The energy transfer element 145*b* and the fluid in pump chamber 138B can transfer energy in the same manner.

The heat transfer between the energy transfer elements 145a, 145b located on the piston heads 134N, 134B' and the fluid within the pump chambers 138A, 138B can be substantially effective for one or more reasons. For example, the ratio of the energy transfer element's surface area to the fluid volume in this location is advantageously high. In addition, the duration for potential heat transfer between the energy transfer element and the fluid is advantageously high because of stagnation-point flow existing in this location during the protraction of the piston heads 134N, 134B'. In some embodiments, the compliant film 151A is especially configured for conducting heat energy. For example, in some embodiments the compliant film 151A can be partially or fully metallic, or otherwise well-suited for conducting heat energy. While certain embodiments have been described, other embodiments are possible, and are within the scope of this disclosure.

Figure 8:
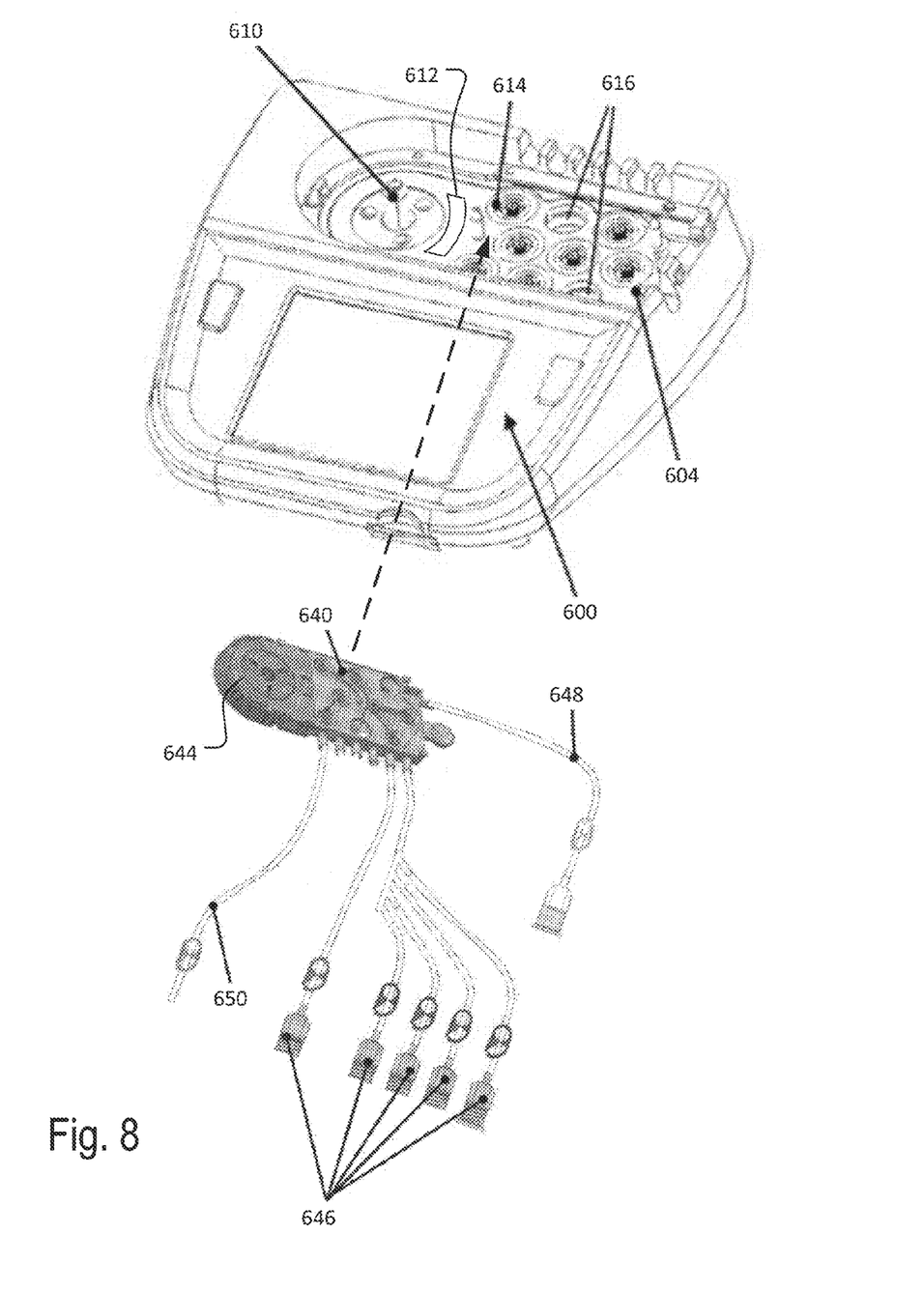
FIG. 8 is a perspective view of another PD system.

While thermoelectric modules have been described as being incorporated into or used in combination with the types of PD machines described above, it should be understood that the thermoelectric modules can be incorporated into or used in combination with various other types of PD machines. As shown in FIG. 8, for example, a PD machine 600 includes a thermoelectric module 612 that is arranged to be adjacent a cassette 640 while the cassette 640 is received within a compartment 604 of the PD machine 600. The thermoelectric module 612 is thereby arranged to effectuate energy transfer with a dialysis fluid in a fluid flow path of the cassette 640.

While the PD machines described above pump dialysate using the substantially hemispherical piston heads 134A, 134B that reciprocate in relation to the pump chambers 138A, 138B of the cassette 112, the PD machine 600 includes a rotary drive shaft 610 that couples with a peristaltic pump 644 that is integral with the cassette 640. Rotation of the drive shaft 610 drives rotation of the peristaltic pump 644 which, in turn, pumps dialysate through the cassette 640 and associated lines. For example, by activating various valve actuators 614, dialysate can be pumped by the peristaltic pump 644 from PD solution bag lines 646, through the cassette 640 (where the dialysate can be heated and/or cooled by the thermoelectric module 612), and into a patient line 648 connected to the patient. In another example, valve actuators 614 can be activated such that dialysate can be pumped by the peristaltic pump 644 from the patient line 648 to a drain line 650. In some embodiments, the PD machine 600 also includes one or more pressure sensors 616 that interface with the cassette 640.

While the depicted embodiments include a single zone at which heating or cooling is applied to the dialysate, in some embodiments, two or more such zones are included in the machine or system. Moreover, while the depicted embodiment of PD machine 102 includes two energy transfer elements 140a, 140b (FIG. 2), some embodiments include a single energy transfer element or more than two energy transfer elements. Additionally, in some embodiments one or more of the energy transfer element(s) depicted in one embodiment can be combined with one or more of the energy transfer element(s) depicted in another embodiment. For example, in some embodiments the energy transfer elements 140a and/or 140b can be combined with the energy transfer elements 145a and/or 145b (FIG. 6) in a single PD machine embodiment.

In the depicted embodiment of PD machine 102, the fluid temperature sensor 144 is located adjacent to the cassette 112 near where the dialysate exits the cassette 112 and enters the patient line 130, in some embodiments, the fluid temperature sensor 144 can be located elsewhere including, but not limited to, on the patient line 130 or other locations adjacent to the cassette 112. In some embodiments, one or more temperature sensors can be alternatively or additionally positioned in other places within the machine or system. For example, in some embodiments a temperature sensor can be positioned prior to the zone(s) at which heating or cooling is applied to the dialysate. In some embodiments, one or more temperature sensors can be placed along the patient line 130. In some embodiments, a first temperature sensor can be positioned prior to the zone(s) at which heating or cooling is applied, and a second temperature sensor can be positioned after the zone(s) at which heating or cooling is applied.

While the temperature control device 300 is described above as being in communication with the PD machine 202 via a cable 360, in some embodiments the temperature control device 300 and the PD machine 202 can communicate wirelessly. Moreover, in some embodiments the temperature control device 300 can operate independently of the PD machine 202 (i.e., without communicating with the PD machine 202, or without receiving control communications from the PD machine 202).

While the thermoelectric modules that are arranged to control the temperature of dialysate in the fluid flow path of the cassettes described above have been described as being part of a PD system, these types of thermoelectric modules can be used in any of various other types of cassette-based medical fluid pumping systems, including hemodialysis systems. Moreover, while the fluid flow paths in the zone(s) at which heating or cooling is applied have been depicted as serpentine flow paths, other types of flow paths can be used in the zone(s) at which heating or cooling is applied. Such flow paths can include, but are not limited to, linear, spiral, broadened, bifurcated, and the like. In some embodiments, heat transfer rates can be enhanced by including features such as fins, static mixers, and the like.

While the PD machines 102, 102', 202 have been described as including a touch screen and associated buttons, the PD machines 102, 102', 202 can include other types of screens and user data entry systems, as well as any user interface that is separate from, but in communication with, the PD machine 102, 102', 202, (e.g., a smartphone, tablet, smart watch, or other mobile device). In certain implementations, for example, the PD machines 102, 102', 202 includes a display screen with buttons (e.g., feathertouch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

While certain systems have been described that use prepackaged dialysis solutions, online dialysis solution generation can alternatively or additionally be used in conjunction with some embodiments described herein. Such online dialysis solution generation can supply an as-needed continuous flow of dialysis solution, thereby eliminating the need to prepare a batch of dialysate that is stored in bags (e.g., bags 122 as shown in FIGS. 1 and 3) for later use. In some such embodiments, bicarbonate buffered dialysate can be generated on demand by filtering tap water (e.g., using a reverse osmosis technique) and then injecting a bicarbonate concentrate and an acid concentrate into the filtered water to make the dialysis solution that is then delivered to the patient's peritoneal cavity.

While many of the systems described herein simply route spent dialysate to a drain for disposal, dialysis solution regeneration devices, such as sorbent cartridges, can be used in conjunction with some embodiments described herein. For example, sorbent cartridges capable of removing uremic toxins can be used to clean spent dialysate so it can be used again. In some embodiments, the sorbent cartridge can purify water and regenerate spent dialysis solution through the use of a series of layers which can remove heavy metals (e.g., lead, mercury, arsenic, cadmium, chromium and thallium), oxidants (e.g., chlorine and chloramine), urea, phosphate and other uremic waste metabolites (e.g., creatinine and uric acid) from the solution, without removing or adsorbing excessive amounts of cations (e.g., calcium, magnesium, sodium, potassium) or essential ions. In some implementations, the components of the cartridge that perform the afore-mentioned functions include a purification layer that includes activated carbon; an ion exchange layer that includes a polymer phosphate binder or an ion exchange sorbent; and a urea removal layer that includes strong acid cation exchange resin and basic resin(s) or urea-degrading enzymes and an ion exchange sorbent together with a composition that rejects cations (e.g., flat membrane/hollow fibers described further herein, an ion-exchange membrane, or an encapsulation surrounding the urea removal components).

One or more features from the embodiments described herein can be combined with one or more features of one or more other embodiments described herein to result in hybrid embodiments that are within the scope of this disclosure. For example, the PD machine 102 with energy transfer elements 140a, 140b and the temperature sensors 143, 144 can be used in combination with a separate temperature control device 300.

What is claimed is:

1. A peritoneal dialysis machine comprising:
   a console including a compartment configured to releasably receive a dialysis fluid cassette, the console including one or more thermoelectric modules arranged to be adjacent the cassette while the cassette is received by the compartment and to effectuate energy transfer with a dialysis fluid in a fluid flow path of the cassette that is adjacent the one or more thermoelectric modules;
   a fluid temperature sensor arranged adjacent to the cassette while the cassette is received by the compartment, the fluid temperature sensor arranged near where the dialysis fluid exits the cassette to enter a patient line extending from the cassette and arranged to detect a temperature of the dialysis fluid after being affected by the one or more thermoelectric modules;
   one or more processors coupled to the console and configured to control the one or more thermoelectric modules based on the temperature of the dialysis fluid detected by the fluid temperature sensor such that: (i) during a heating mode the one or more thermoelectric modules heat the dialysis fluid in the fluid flow path of the cassette and (ii) during a cooling mode the one or more thermoelectric modules cool the dialysis fluid in the fluid flow path of the cassette; and
   an ambient temperature sensor arranged to detect an ambient temperature around the console,
   wherein the one or more processors are configured to determine, based on the ambient temperature detected by the ambient temperature sensor, a target temperature for the dialysis fluid as measured by the fluid temperature sensor, and
   wherein the target temperature is determined based on an anticipated change in the temperature of the dialysis fluid as the dialysis fluid flows from the peritoneal dialysis machine through the patient line to a patient receiving treatment from the peritoneal dialysis machine.

2. The peritoneal dialysis machine of claim 1, wherein the one or more processors are configured to control the one or more thermoelectric modules based on the ambient temperature detected by the ambient temperature sensor.

3. The peritoneal dialysis machine of claim 1, wherein the fluid temperature sensor is a first fluid temperature sensor, and wherein the peritoneal dialysis machine further comprises a second fluid temperature sensor located to detect the temperature of the dialysis fluid prior to being affected by the one or more thermoelectric modules.

4. The peritoneal dialysis machine of claim 3,
   wherein the one or more processors are configured to control the one or more thermoelectric modules based on the temperatures of the dialysis fluid detected by the first fluid temperature sensor and the second fluid temperature sensor.

5. The peritoneal dialysis machine of claim 1, further comprising first and second movable piston heads, wherein the first and second movable piston heads are movable in a direction substantially perpendicular to the cassette.

6. The peritoneal dialysis machine of claim 1, wherein the peritoneal dialysis machine is adapted to be connected to a supply of water and to a source of concentrate and to generate the dialysis fluid using the water and the concentrate.

7. The peritoneal dialysis machine of claim 1, wherein the one or more processors are configured to control the one or more thermoelectric modules based on the target temperature.

8. The peritoneal dialysis machine of claim 1, wherein the target temperature is determined to be greater than 37° C. based on the ambient temperature detected by the ambient temperature sensor being less than 37° C.

9. The peritoneal dialysis machine of claim 1, wherein the target temperature is determined to be less than 37° C. based on the ambient temperature detected by the ambient temperature sensor being greater than 37° C.

10. The peritoneal dialysis machine of claim 1, wherein the anticipated change in the temperature of the dialysis fluid as the dialysis fluid flows from the peritoneal dialysis machine through the patient line to the patient is determined based on a measured temperature of spent dialysate emptying from the patient in a drain line at a distance from the patient.

11. The peritoneal dialysis machine of claim 10, wherein the distance from the patient is equal to a length of the patient line.

* * * * *